(12) United States Patent
Petersen

(10) Patent No.: US 11,413,368 B2
(45) Date of Patent: Aug. 16, 2022

(54) BINARY ODOR CONTROL SYSTEM FOR ABSORBENT ARTICLES

(71) Applicant: INTERNATIONAL PAPER COMPANY, Memphis, TN (US)

(72) Inventor: Brent A. Petersen, Seattle, WA (US)

(73) Assignee: INTERNATIONAL PAPER COMPANY, Memphis, TN (US)

(*) Notice: Subject to any disclaimer, the term of this patent is extended or adjusted under 35 U.S.C. 154(b) by 383 days.

(21) Appl. No.: 15/636,576

(22) Filed: Jun. 28, 2017

(65) Prior Publication Data

US 2017/0296693 A1 Oct. 19, 2017

Related U.S. Application Data

(63) Continuation of application No. 14/143,093, filed on Dec. 30, 2013, now Pat. No. 9,717,817.

(51) Int. Cl.
*A61F 13/15* (2006.01)
*A61L 15/18* (2006.01)
(Continued)

(52) U.S. Cl.
CPC ........ *A61L 15/18* (2013.01); *A61F 13/15626* (2013.01); *A61F 13/534* (2013.01); *A61F 13/539* (2013.01); *A61F 13/8405* (2013.01); *A61L 15/20* (2013.01); *A61L 15/28* (2013.01); *A61L 15/46* (2013.01); *A61L 15/60* (2013.01); *A61F 2013/530065* (2013.01); *A61F 2013/530481* (2013.01);
(Continued)

(58) Field of Classification Search
CPC .......... A61L 15/18; A61L 15/28; A61L 15/46; A61L 15/60; A61L 2300/11; A61F 13/534; A61F 13/539; A61F 13/8405; A61F 2013/530481; A61F 2013/8408; A61F 2013/8414; A61F 2013/8426
USPC ........................................ 604/359, 360, 367
See application file for complete search history.

(56) References Cited

U.S. PATENT DOCUMENTS 3,794,034 A 2/1974 Jones, Sr.
3,975,222 A 8/1976 Mesek
(Continued)

FOREIGN PATENT DOCUMENTS

CN 101868258 A 10/2010
CN 101903048 A 12/2010
(Continued)

OTHER PUBLICATIONS

Japanese Office Action dated Dec. 7, 2016, issued in corresponding Japanese Application No. 2014-214751, filed Oct. 21, 2014, 14 pages.
(Continued)

*Primary Examiner* — Jacqueline F Stephens
(74) *Attorney, Agent, or Firm* — Thomas W. Barnes, III; Clifford R. Lamar, II

(57) ABSTRACT

Cellulosic pulp structures integrating unreacted quantities of an inorganic peroxide and a destabilizing acid, as binary components of an odor control system, absorbent articles incorporating such structures, and various methods of forming the same, are disclosed herein. The components are adapted to react in the presence of an aqueous fluid to produce hydrogen peroxide, thereby providing an antimicrobial and odor mitigating effect.

21 Claims, 1 Drawing Sheet

(51) Int. Cl.
  *A61L 15/28* (2006.01)
  *A61L 15/60* (2006.01)
  *A61F 13/84* (2006.01)
  *A61L 15/46* (2006.01)
  *A61F 13/534* (2006.01)
  *A61F 13/539* (2006.01)
  *A61L 15/20* (2006.01)
  *A61F 13/53* (2006.01)

(52) U.S. Cl.
  CPC ........... *A61F 2013/8408* (2013.01); *A61F 2013/8414* (2013.01); *A61F 2013/8426* (2013.01); *A61L 2300/11* (2013.01); *Y10T 29/49801* (2015.01)

(56) References Cited

U.S. PATENT DOCUMENTS

| | | | |
|---|---|---|---|
| 4,363,322 A * | 12/1982 | Andersson | A61F 13/00029 604/377 |
| 4,447,243 A | 5/1984 | Claiborne | |
| 4,865,855 A | 9/1989 | Hansen | |
| 4,980,294 A | 12/1990 | Elias et al. | |
| 5,137,537 A | 8/1992 | Herron | |
| 5,281,207 A | 1/1994 | Chmielewski et al. | |
| 5,300,192 A | 4/1994 | Hansen et al. | |
| 5,308,896 A | 5/1994 | Hansen et al. | |
| 5,352,480 A | 10/1994 | Hansen et al. | |
| 5,447,977 A | 9/1995 | Hansen | |
| 5,547,541 A | 8/1996 | Hansen et al. | |
| 5,547,745 A | 8/1996 | Hansen et al. | |
| 5,571,618 A | 11/1996 | Hansen et al. | |
| 5,589,256 A | 12/1996 | Hansen et al. | |
| 5,607,759 A | 3/1997 | Hansen et al. | |
| 5,609,727 A | 3/1997 | Hansen et al. | |
| 5,614,570 A | 3/1997 | Hansen | |
| 5,618,855 A | 4/1997 | Noda | |
| 5,641,561 A | 6/1997 | Hansen et al. | |
| 5,672,418 A | 9/1997 | Hansen et al. | |
| 5,693,411 A | 12/1997 | Hansen et al. | |
| 5,749,863 A | 5/1998 | Payne | |
| 5,789,326 A | 8/1998 | Hansen et al. | |
| 5,807,364 A | 9/1998 | Hansen | |
| 5,817,300 A | 10/1998 | Cook et al. | |
| 5,998,032 A | 12/1999 | Hansen et al. | |
| 6,068,620 A | 5/2000 | Chmielewski | |
| 6,071,549 A | 6/2000 | Hansen | |
| 6,080,908 A | 6/2000 | Guarracino et al. | |
| 6,187,990 B1 | 2/2001 | Runeman et al. | |
| 6,231,721 B1 | 5/2001 | Quick | |
| 6,340,411 B1 | 1/2002 | Hansen | |
| 6,395,395 B1 | 5/2002 | Hansen et al. | |
| 6,425,979 B1 | 7/2002 | Hansen et al. | |
| 6,436,418 B1 | 8/2002 | Sheldon et al. | |
| 6,461,553 B1 | 10/2002 | Hansen et al. | |
| 6,509,284 B1 | 1/2003 | Quincy, III | |
| 6,521,087 B2 | 2/2003 | Hansen | |
| 6,521,339 B1 | 2/2003 | Hansen et al. | |
| 6,596,103 B1 | 7/2003 | Hansen et al. | |
| 6,627,249 B2 | 9/2003 | Hansen | |
| 6,638,884 B2 | 10/2003 | Quick et al. | |
| 6,652,845 B2 | 11/2003 | Hu et al. | |
| 6,719,862 B2 | 4/2004 | Quick et al. | |
| 6,767,553 B2 | 7/2004 | Sun et al. | |
| 6,852,904 B2 | 2/2005 | Sun et al. | |
| 6,967,025 B2 | 11/2005 | DiCintio et al. | |
| 7,018,490 B2 | 3/2006 | Hansen | |
| 7,144,474 B1 | 12/2006 | Hansen et al. | |
| 7,175,741 B2 | 2/2007 | West et al. | |
| 7,235,263 B2 | 6/2007 | Koenig et al. | |
| 8,753,484 B2 | 6/2014 | Tan | |
| 9,717,817 B2 | 8/2017 | Petersen | |
| 2002/0018761 A1 | 2/2002 | Moscherosch | |
| 2003/0124171 A1 | 7/2003 | Sun et al. | |
| 2003/0144637 A1 | 7/2003 | Sun et al. | |
| 2004/0120921 A1 | 6/2004 | Quincy, III et al. | |
| 2004/0122386 A1* | 6/2004 | Mocadlo | A61F 13/84 604/359 |
| 2004/0172001 A1 | 9/2004 | Tenberg et al. | |
| 2004/0266302 A1 | 12/2004 | DiSalvo et al. | |
| 2006/0029567 A1* | 2/2006 | Dutkiewicz | D06M 13/342 424/76.1 |
| 2006/0088498 A1 | 4/2006 | Martin et al. | |
| 2007/0077428 A1 | 4/2007 | Hamed | |
| 2007/0142799 A1 | 6/2007 | Ales et al. | |
| 2007/0149716 A1 | 6/2007 | Funk et al. | |
| 2008/0058739 A1 | 3/2008 | Roberts et al. | |
| 2009/0069181 A1 | 3/2009 | Boulos | |
| 2009/0105676 A1* | 4/2009 | Brusk | A61F 13/8405 604/359 |
| 2010/0262098 A1 | 10/2010 | Brusk et al. | |
| 2011/0015596 A1* | 1/2011 | Wastlund-Karlsson | A61L 15/28 604/359 |
| 2011/0054430 A1 | 3/2011 | Waestlund-Karlsson | |
| 2011/0182845 A1 | 7/2011 | Braig et al. | |
| 2012/0079989 A1* | 4/2012 | Adamy | A01K 1/0154 119/173 |
| 2013/0269890 A1 | 10/2013 | Dougherty, Jr. | |
| 2014/0093471 A1 | 4/2014 | Porter et al. | |
| 2015/0182655 A1 | 7/2015 | Petersen | |
| 2016/0151257 A1 | 6/2016 | Klingman | |
| 2017/0172152 A1 | 6/2017 | Tan et al. | |

FOREIGN PATENT DOCUMENTS

| | | |
|---|---|---|
| CN | 102791298 A | 11/2012 |
| EP | 1 034 801 A1 | 3/1999 |
| EP | 1 034 803 A1 | 9/2000 |
| EP | 1358894 A1 | 11/2003 |
| EP | 1470827 A2 | 10/2004 |
| EP | 2491910 A1 | 8/2012 |
| JP | S5285600 A | 7/1977 |
| JP | S56160974 A | 12/1981 |
| JP | H11-508327 A | 7/1999 |
| JP | 2003-523484 A | 8/2003 |
| JP | 2007-538059 A | 12/2007 |
| JP | 2008-048775 A | 3/2008 |
| JP | 2013-010006 A | 1/2013 |
| JP | 2016169446 A | 9/2016 |
| KR | 20090046623 A | 5/2009 |
| KR | 101857746 B1 | 5/2018 |
| WO | 03/051410 A1 | 12/2001 |
| WO | 03/051413 A1 | 6/2003 |
| WO | 2003051414 A1 | 6/2003 |
| WO | WO-2003051410 A1 | 6/2003 |
| WO | 03/053487 A1 | 7/2003 |
| WO | WO-2004110876 A1 | 12/2004 |
| WO | WO-2007149590 A2 | 12/2007 |
| WO | WO-2008058563 A1 | 5/2008 |
| WO | WO-2008138386 A1 | 11/2008 |
| WO | 2009/066255 A2 | 5/2009 |
| WO | WO-2009111768 A1 | 9/2009 |
| WO | WO-2010088064 A2 | 8/2010 |
| WO | 2011/092098 A1 | 8/2011 |
| WO | WO-2011103183 A1 | 8/2011 |
| WO | 2012/044896 A1 | 4/2012 |
| WO | WO-2014052055 A1 | 4/2014 |
| WO | WO-2015048427 A1 | 4/2015 |
| WO | WO-2015133267 A1 | 9/2015 |
| WO | WO-2016143217 A1 | 9/2016 |

OTHER PUBLICATIONS

Japanese Office Action dated Jan. 26, 2016, issued in corresponding Japanese Application No. 2014-214751, filed Oct. 21, 2014, 10 pages.

Communication Pursuant to Article 94(3) EPC, dated Nov. 2, 2016, issued in corresponding European Application No. 14 191 365.7, filed Oct. 31, 2014, 6 pages.

(56) References Cited

OTHER PUBLICATIONS

Notification of First Office Action dated Jun. 28, 2016, issued in Chinese Patent Application No. 201410749321.1, filed Dec. 9, 2014, with partial English Translation, 16 pages.
Japanese Office Action dated Jul. 5, 2018, issued in corresponding Japanese Application No. 2017-075350, filed Oct. 21, 2014, 11 pages.
Examination Report dated Jul. 18, 2018, issued in corresponding Indian Application No. 3105/DEL/2014, filed Oct. 30, 2014, 4 pages.
Japanese Office Action dated Jul. 2, 2018, issued in corresponding Japanese Application No. 2014-214751, filed Oct. 21, 2014, 18 pages.
Communication (Extended Search Report) dated Oct. 23, 2019, issued in corresponding European Application No. 19185867.9, filed Oct. 30, 2014, 6 pages.
Notification of First Office Action dated Jul. 3, 2020, issued in Chinese Application No. 201711164813.4, filed Dec. 9, 2014, 17 pages.
Tsuchiya et al., "A new color test for the measurement of freshness offish by volatile bases estimation", Tohoku journal of agricultural research, 1954, vol. 5(1), pp. 37-46.
A. Brzezinski, et al., Efficacy of a Novel ph-Buffering Tampon in Preserving the Acidic Vaginal pH During Menstruation, International Journal of Gynecology and Obstetrics, Jun. 2004, pp. 298-300, vol. 85 issue 3.
Examination Report dated Apr. 23, 2019, in AU Application No. 2018204635, filed May 25, 2018, 16 pages.
Examination Report dated Jul. 26, 2019, in U Application No. 2018204635, filed May 25, 2018, 11 pages.
Examination Report dated Oct. 9, 2019, in Australian Application No. 2019208150, filed May 25, 2018, 8 pages.
Examination Report dated Sep. 28, 2020, in Australian Application No. 2019208150, filed May 25, 2018, 5 pages.
International Search Report and Written Opinion dated Feb. 20, 2019, issues in corresponding Application No. PCT/US2018/034759, Filed May 25, 2018, 23 pages.
T. Yasuhiko, et al., A new Color Test for the Measurement of Freshness of Fish by Valatile Bases Estimation, Tohoku Journal of Agriculture Research, Sep. 20, 2954, pp. 37-46, 5(1), http://hdl.handle.net/10097/29122.
Y. Liu, et al., Heterogeneous Uptake of Amines by Citric Acid and Humic Acid, Environmental Science and Technology American Chemical Society, 2012, pp. 1112-1118.

\* cited by examiner

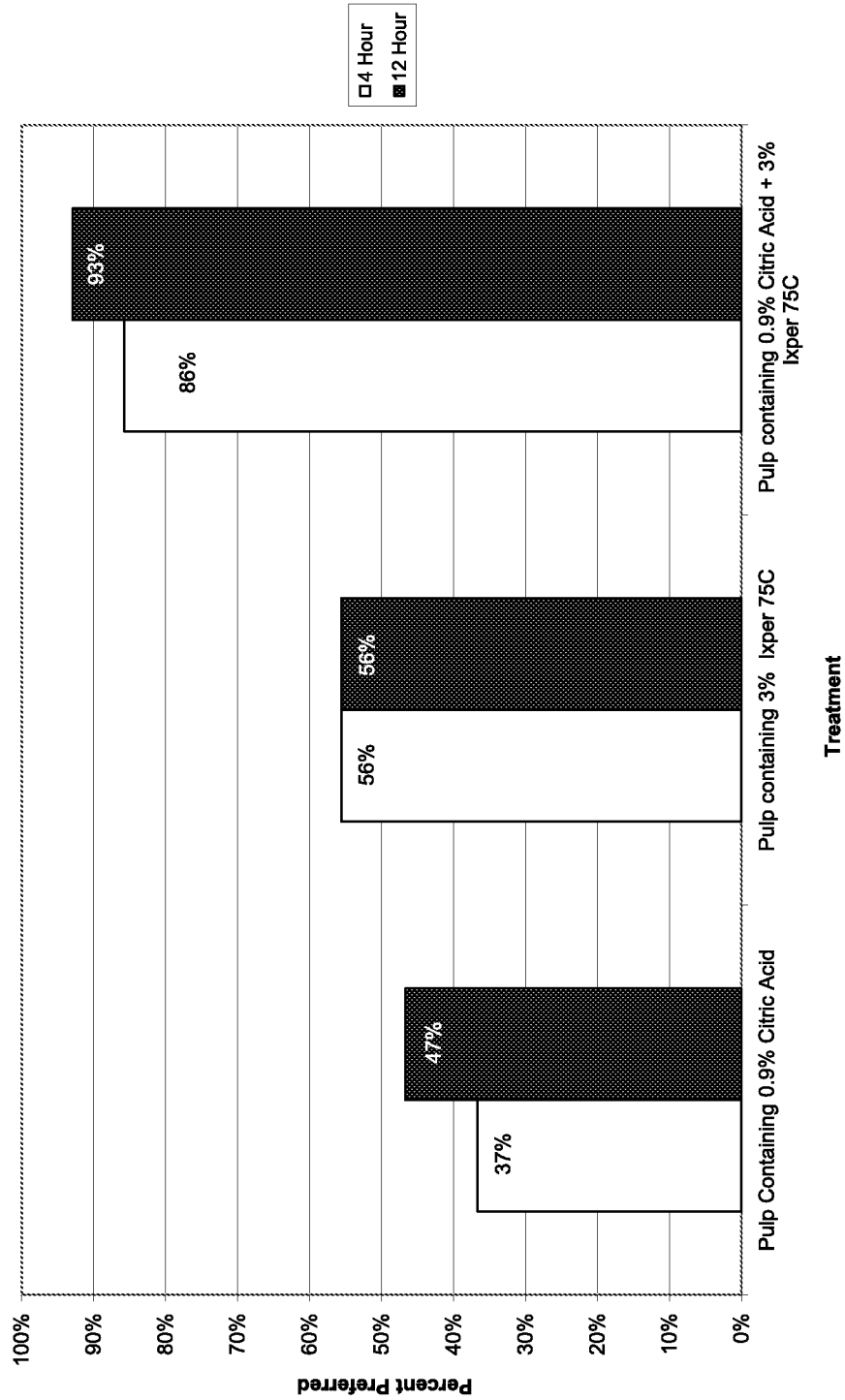

BINARY ODOR CONTROL SYSTEM FOR ABSORBENT ARTICLES

CROSS REFERENCE TO RELATED APPLICATION

This application is a continuation of U.S. patent application Ser. No. 14/143,093, filed Dec. 30, 2013, which is expressly incorporated herein by reference in its entirety.

TECHNICAL FIELD

This disclosure relates to odor control in absorbent articles, and in particular to cellulosic pulp structures integrating binary components of an odor control system that are adapted to react in the presence of an aqueous fluid to produce hydrogen peroxide, absorbent articles incorporating such structures, and various methods of forming the same.

BACKGROUND

Odor has long been a challenge with absorbent articles such as diapers, adult incontinent products, feminine hygiene products, as well as bandages, wound dressings, and other such items. These articles are designed to contain body or physiological waste materials, which generally take the form of fluids (such as blood, urine, perspiration, etc.). There are odors associated with these waste materials, such as due to microbial activity (on urea in urine, on protein and lipids in blood, etc.) and so forth, and there have been many attempts to reduce or eliminate such odors. Such attempts generally fall into one of three categories. One is the use of added materials to absorb or adsorb volatile odors in an effort to restrict their release to the surrounding environment. Another is the use of masking materials such as perfumes. A third is the use of substances to inhibit the production of bodily fluid degradation products.

Many absorbent articles are configured to include a fluid absorbent core disposed between a top sheet and a back sheet. The top sheet is typically formed from a fluid-permeable material adapted to promote fluid transfer into the absorbent core, such as upon a fluid insult, usually with minimal fluid retention by the top sheet. Accordingly the top sheet material may be hydrophobic. The absorbent core is adapted to retain fluid, and the back sheet is typically formed from a fluid-impermeable material to form a barrier to prevent retained fluid from escaping. The absorbent core may consist of one or more layers, such as layers to acquire, distribute, and/or store fluid. In many cases, a matrix of cellulose fibers, such as in the form of an airlaid pad and/or non-woven web, is used in (or as) the absorbent core of absorbent articles. In some cases, the different layers may consist of one or more different types of cellulose fibers, such as cross-linked cellulose fibers. The absorbent core may also include one or more fluid retention agents, such as a superabsorbent polymer, distributed throughout the fiber matrix.

Whatever the structure, there continues to be a need for effective odor control in a wide range of absorbent articles. A robust odor control system would not only eliminate odors present at the time of fluid insult, but also arrest the generation of subsequent odors.

SUMMARY

Inorganic peroxides, and in particular alkaline earth metal peroxides such as calcium peroxide, magnesium peroxide, and so forth, are known for bleaching, disinfecting, and deodorizing. Such reagents release hydrogen peroxide ($H_2O_2$) upon contact with a hydrous fluid. Different inorganic peroxides have different hydrogen peroxide release profiles, but many display higher degrees of $H_2O_2$ release at lower pH values. Although not wishing to be bound by theory, lower pH values are also believed to increase the stability of the $H_2O_2$ that is generated and enhance its effectiveness for odor mitigation.

Accordingly, a robust odor control system as described above may be provided by incorporating a stable inorganic peroxide (e.g., calcium peroxide), and a destabilizing acid (e.g., citric acid), in an absorbent article, such as in a cellulosic pulp structure that forms at least part of an absorbent core of an absorbent article, in accordance with the present disclosure. Such a system is referred to herein as a peroxide-based binary odor control system, or more simply as a binary odor control system. In some embodiments, the cellulosic pulp structure is defined by a matrix of cellulose fibers that have been treated with the components of the binary odor control system. In use, when the inorganic peroxide on the cellulose fibers is contacted by a body waste material (such as urine or another fluid, etc.) that has been acidified, the peroxide will become destabilized, and through oxidative means will neutralize odors and provide an antimicrobial effect.

Thus, in accordance with the present disclosure, various embodiments of absorbent articles and/or cellulosic pulp structures that incorporate a peroxide-based binary odor control system, as well as methods for producing such articles and/or structures, are presented herein.

For example, in some embodiments constructed in accordance with the present disclosure, an absorbent article includes a cellulosic pulp structure defined by a matrix of cellulose fibers and being adapted to acquire and retain fluid, wherein the cellulose fibers are treated with an inorganic peroxide and a destabilizing acid adapted to react with the inorganic peroxide in the presence of an aqueous fluid to produce hydrogen peroxide.

Some of such embodiments may include a fluid retention agent, such as superabsorbent polymer (or "SAP") distributed through the cellulosic pulp structure. In some embodiments, the cellulosic pulp structure may be disposed between a fluid-permeable top sheet and a fluid-impermeable back sheet. In some, the cellulosic pulp structure forms, includes, and/or is included in one or more of multiple layers of an absorbent core in the absorbent article, such as a storage layer and an additional layer (variously called an "acquisition and distribution layer", "A/D layer", or "ADL") interposed between the storage layer and the top sheet, which is adapted to acquire fluid and to distribute acquired fluid to the storage layer. In some of such embodiments, the storage layer may be treated with the peroxide and the A/D layer may be treated with the acid. In some of such embodiments, the storage layer is treated with both components. Some embodiments may include cross-linked cellulose fibers.

In some embodiments of a method of forming an odor-controlling cellulosic pulp structure and/or an absorbent article incorporating such a structure, a cellulosic pulp structure is formed by first forming a cellulose pulp sheet from a cellulose pulp slurry, and then forming a matrix of cellulose fibers from the cellulose pulp sheet. An inorganic peroxide and a destabilizing acid are separately added while forming the cellulosic pulp structure so that suitable amounts are retained in the matrix of cellulose fibers to react to form hydrogen peroxide in the presence of a fluid insult.

In some methods, the inorganic peroxide is added during forming the pulp sheet. In some methods, the destabilizing acid is added by applying the acid in aqueous form to the pulp sheet. In some methods, a fluid retention agent is distributed through the matrix of cellulose fibers. In some of such methods, the peroxide, in particulate form, is also distributed through the matrix of cellulose fibers.

The concepts, features, methods, and component configurations briefly described above are clarified with reference to the accompanying drawings and detailed description below.

BRIEF DESCRIPTION OF THE DRAWINGS

The FIGURE is a graph showing results of an evaluation of odor control efficacy of cellulosic pulp structures integrating binary components of an odor control system, constructed in accordance with the present disclosure, in comparison with controls.

DETAILED DESCRIPTION

Cellulose pulp suitable for the embodiments disclosed herein may be made using conventional kraft, sulfite, or other well-known processes. The furnish can be from any of various cellulose containing raw materials. Usually, these are deciduous hardwoods, coniferous species (usually termed softwoods), or mixtures of these materials, but this disclosure is not so limited. Due to its suitability for use in absorbent cores of diapers and like products, a bleached softwood kraft pulp that would normally be produced for ultimate use as absorbent fluff may be used. For example, suitable cellulosic fibers produced from southern pine that are usable with the present invention are available from Weyerhaeuser Company under the designations CF416, NF405, PL416, FR416, NB416, and so forth. So-called "dissolving pulps" may be used, but may not be optimal due to their low process yield and resultant greater cost. The present disclosure includes all of such raw materials and mixtures thereof.

A cellulose pulp sheet may be produced in a "wet laying" process, a preparation of the sheet or web from a suspension of pulp fibers in water by conventional papermaking techniques causing the fibers to hydrogen bond together. In an example process, wood chips are digested with chemicals to form cellulosic wood pulp fibers which can then be washed and bleached if desired. The fibers are then formed into an aqueous slurry which is delivered from a headbox to a wire screen. Water is drawn from the deposited pulp by a vacuum system, leaving a deposited pulp sheet that is further dewatered by pressure rolls. The pulp sheet is then dried and then wound into a roll for shipment. Rolls produced in this fashion typically have a moisture content of 10% or less (and in many cases no more than about 8% or 6%) by weight of the fibers.

To form an absorbent core for an absorbent article, and in particular a disposable absorbent article such as a diaper, adult incontinent product, feminine hygiene product, and so forth, the rolls may then be fiberized, such as by feeding the rolls into a hammermill, to produce fiberized cellulose in a form referred to as "fluff." The fluff is then formed into pads, such as via an airlaid process or otherwise, for inclusion in the absorbent article. U.S. Pat. No. 3,975,222, to Mesek, is representative of such a process.

As noted above, such articles may have a top sheet through which fluid will flow, the absorbent core, and a fluid impermeable back sheet. The absorbent core may have one or more layers. For example, the absorbent core may have a storage layer adapted to retain fluid, as well as one or more layers that are, individually or collectively, adapted to acquire and/or distribute fluid received through the top sheet. Such layers are sometimes referred to as acquisition and/or distribution layers. The different layers may have different amounts and types of cellulose fibers as appropriate to the intended function. Each layer may incorporate individualized pulp fibers along with other material, such as crosslinked cellulose fibers, superabsorbent particles and/or other fluid retention agents, and so forth. For example, storage layers for incorporation into diapers typically include superabsorbent particles. An example disposable diaper structure is disclosed, for example, in U.S. Pat. No. 6,436,418, to Sheldon.

The components of the binary odor control system according to the present disclosure, and/or any other additives (such as to facilitate retention of the components on the fibers, etc.), may be applied to the cellulose fibers in any suitable manner, for example at the wet end by addition of one or more of the components into the headbox before formation of the pulp sheet in order to incorporate the components into the pulp sheet, by application to the formed pulp sheet before or after drying, by application to the fiberized pulp, etc.

However, one challenge in application is that the binary odor control system components will react with each other in an aqueous medium, and therefore methods according to the present disclosure incorporate the components into the cellulosic pulp structure in a manner that provides sufficient amounts of unreacted components to produce hydrogen peroxide upon the structure receiving a fluid insult.

In an example method, the inorganic peroxide is added upstream of the forming section of a pulp drying machine, such as to the pulp slurry. Alternatively (or additionally), the inorganic peroxide is added to the formed sheet in a size press. After drying, a solution of the destabilizing acid is drizzled onto the sheet in discrete lines. The amounts of the reagents are optimized toward the intended effect, e.g., the duration and/or amount of hydrogen peroxide production upon receiving a fluid insult, and take into account the application process. For example, the amount of peroxide applied to the sheet accounts for the portion consumed upon the subsequent application of the acid, and the acid strength and/or quantity is sufficient so that it is not depleted after neutralizing the peroxide where the components overlap.

In another example method, both components may be separately drizzled onto the pulp sheet after drying, such as in discrete, alternating lines.

Yet another example method incorporates the components in separate manufacturing steps, such as may be the case in settings in which the cellulosic pulp structure is formed at a facility or on a machine separate from the production of the pulp sheet. In such a method, one component (such as the acid, such as citric acid) is added to the pulp sheet, whereas the other component (such as the peroxide, such as calcium peroxide) is added to the pulp after fiberization and/or during formation of the cellulosic pulp matrix. This approach may be suitable when the cellulosic pulp matrix is (or includes, or forms a part of) an airlaid pad to which SAP particles are added, for example by adding calcium peroxide in powder form along with the SAP. Such a method may be particularly suitable to the nature of one or more of the components. For example, calcium peroxide is insoluble in water, which may practically limit (and/or increase the cost of) available application methods.

An example method of incorporating calcium peroxide into the cellulose fibers in sheet form is to form the peroxide in situ, for example by adding calcium hydroxide to the pulp at some point prior to drying, then treating the dried pulp sheet with hydrogen peroxide to yield calcium peroxide.

In yet another example method, the components may be incorporated in separate layers of a multi-layer absorbent core structure. For example, in embodiments in which the cellulosic pulp structure forms, includes, or is included in one or more of multiple layers of the absorbent core, such as a storage layer as well as an additional layer (e.g., an acquisition and/or distribution layer) interposed between the storage layer and the top sheet, the storage layer may incorporates the peroxide, whereas the additional layer may incorporate the destabilizing acid. Optionally, the storage layer may include the treated (i.e., with both components) cellulosic pulp structure.

The aforementioned example application methods are illustrative of any number of suitable application methods, as well as combinations thereof, all of which are understood to be encompassed by the present disclosure.

The following examples describe illustrative, non-limiting embodiments of methods of forming a cellulosic pulp structure incorporating a binary odor control system in accordance with the present disclosure.

Example 1: Treated Sheet Formation

Calcium peroxide is added upstream of the forming section of a pulp drying machine in sufficient quantity to ensure that from about 1% to 10% on a fiber loading basis (i.e., percentage by mass of fibers) is retained in the dried sheet. For example, in some test runs, a quantity of calcium peroxide equivalent to 4% of the mass of the fibers retained in the dried sheet was used. Optionally, a retention aid (such as Nalco 7520, available from Nalco Company of Naperville, Ill.) is added to the pulp slurry. Upon drying and prior to rolling, parallel lines of an aqueous solution of citric acid is drizzled onto the dry sheet by means of a spray bar suspended above the sheet, with nozzles spaced about 0.75" to 1.5" apart, effective to dose about 50% of the sheet surface area. The acid dosage is at a level such that about 0.45% to about 3% free acid remains on a fiber loading basis, which may be accomplished by determining a suitable acid concentration and delivery rate. The component concentrations, equipment configurations (e.g. nozzle spacing, spray pattern), delivery rate (e.g. of the acid), and so forth, may be varied within ranges suitable to leave desired unreacted amounts of the components in sufficient concentrations to effect the production of desired amounts of hydrogen peroxide in use—e.g., when the treated pulp is formed into a cellulosic pulp matrix that is then contacted with an aqueous fluid.

The pulp sheet is dried down to a moisture content of about 6% and the water from the acid solution raises the moisture content back up to about 9%. The treated sheet may then be formed into a cellulosic pulp structure defined by a matrix of treated cellulose fibers that is suitable for use in absorbent articles (including, for example, diapers, adult incontinent products, feminine hygiene products, bandages, and so forth), according to standard methods.

Example 2: Treated Pad Formation

Bleached kraft pulp strips (suitable examples include grades provided by the Weyerhaeuser Company under the designations FR416, NB416, CF416, and so forth) containing 6% moisture, having a basis weight of 750 g/m$^2$, a specific gravity of 0.54, and measuring 18" in the machine direction and 2" in the cross direction, were treated using a syringe filled with a 20% aqueous solution of citric acid (ACS reagent, ≥99.5% obtained from Sigma-Aldrich). The dosage of citric acid was 0.9% of the weight of the pulp.

Pads were then produced from the acid-treated pulp. As noted below in the description of odor control efficacy testing, the pads may be formed to simulate absorbent cores found in diapers or other absorbent products. Thus, pad characteristics such as the ratio of SAP to fibers, basis weight, and so forth, may be adjusted accordingly. In this example, the acid-treated pulp strips were processed in a Kamas hammer mill to substantially singulate the fibers. The fiberized pulp (fluff) was then mixed with Hysorb 8600 superabsorbent polymer (available from BASF) at a ratio of 60:40 SAP to fluff. The SAP/fluff blend was then airlaid to form a 6" diameter pad having a basis weight of 300 g/m$^2$. Particles of IXPER® 75C (75% calcium peroxide, available from Solvay Chemicals) were sprinkled on top of the pad at a level of 3% based on the fiber portion of the pad. The edges of the pad were then folded in to form a circle with a 3" diameter. This smaller dimension/higher basis weight pad was then pressed in a Wabash press to achieve a specific gravity of 0.2.

Pads produced according to the method described in Example 2 were used for odor control efficacy testing and rewet testing. The testing protocols and results are described below.

Odor Control Efficacy Test

The odor control efficacy testing protocol is modeled to simulate the conditions an end user would expect to find in an absorbent article during use. Accordingly, the fiber-to-SAP ratio and pad basis weight are adjusted to mimic that of a product into which the binary odor control system may be incorporated.

Two sets of 3" diameter circular pads are formed, one set using untreated control fibers and the other using fibers treated with the odor control component(s). The pads are placed in 4" tall, 3" interior diameter jars, which are paired, each pair including an untreated pad and a treated pad.

Urine samples are collected from healthy adults and, because urine from healthy individuals is sterile and many odors associated with urine are due to microbial activity, the samples are inoculated with bacteria, agitated, and allowed to stand for several minutes to assure uniform distribution. Suitable bacteria includes those present in human flora that would be reactive in a normal human body temperature range (e.g., about 96°–100° F.). For safety purposes this may be accomplished, for example, by each donor expectorating into the donor's urine sample. Alternately, a composite sample may be inoculated with a suitable bacteria. The pad in each jar is then dosed with an amount of inoculated urine equivalent to approximately 70% of its absorbent capacity, as determined by an initial test. The sample jars are sealed and placed in an incubator at a temperature controlled to approximate normal human body temperature (e.g., about 96°–100° F.). At intervals of 4 and 12 hours total incubation time, the sample jars are removed for evaluation, which is performed by removing the sample jar lid and immediately smelling the head space. The evaluators rank the paired samples, indicating one as "preferred" and the other "not preferred."

Standard nonparametric statistical methods may be used to determine whether one formulation is preferred over another based on test results from a number of test participants. For example, for a trial size of 20 participants, at least 65% must rate a sample as being "preferred" in order to establish a result that is statistically significantly different at 95% confidence with 80% power.

Results of a test panel consisting of 20 evaluators, evaluating three pairs of samples (untreated vs. treated with citric acid only; untreated vs. treated with calcium peroxide only; and untreated vs. treated with both components) are presented in the FIGURE. The results indicate that when treated with citric acid alone, less than half of the test panel evaluated the treated pad as "preferred" (with the remaining portion of the panel evaluating the untreated pad as "preferred")—indeed, most of the test panel "preferred" the untreated pad to that treated with citric acid alone. When treated with calcium peroxide alone, slightly more than half of the test panel evaluated the treated pad as "preferred." However, when evaluating a sample pad treated with both components of the binary odor control system, 86% of the test panel "preferred" the treated pad over the untreated control after 4 hours of incubation, and 93% after 12 hours of incubation.

Rewet Test

Acquisition rate and rewet tests are used in the absorbent product industry to measure the ability of an absorbent sample to accept and retain fluid (synthetic urine is usually used) under simulated in-use conditions of load and pressure. Rewet, in particular, refers to the amount of wetness returned to the surface of the absorbent sample onto an absorbent filter paper.

Rectangular airlaid absorbent pads of dimensions about 4"×4¾", and weighing 8.45 g each, were produced from singulated citric acid treated fibers, to which IXPER® 70C calcium peroxide granules and Hysorb 8600 SAP particles were distributed through the pads during the formation process, following a procedure similar to that described in Example 2. The materials present and their relative amounts, in each pad, were 53.8% pulp, 44.5% SAP, 1.1% calcium peroxide, and 0.7% citric acid. The pads were placed on a flat bench, and each was surmounted by an apertured ADL (acquisition distribution layer) material available from Tredegar Film Products, to form an absorbent sample simulating a multi-layer absorbent core structure. The ADLs had the dimensions 2⅞"×4". Upon the ADLs were placed dosing rings 8.3 cm high having inside diameters of 5.4 cm. Using a separatory funnel, each sample was dosed with 45 mL of 0.9% saline solution, three times. The dosage amount is calculated to be appropriate to the fluid capacity per mass unit of the absorbent sample. The amount of time required for each dose to entirely enter the pad was recorded (acquisition time). After each dose, the dosing rings were removed and the samples were allowed to sit for 10 minutes, after which a weighed stack of filter papers rested upon them and under a 4.45 kg weight (8.9 cm diameter) for 3 minutes. The filter papers were then re-weighed for weight gain to determine the amount of fluid yielded back from the dosed sample, i.e., rewet.

| sample | 1st dose acq time (sec) | rewet (g) | 2nd dose acq time (sec) | rewet (g) | 3rd dose acq time (sec) | rewet (g) | total rewet (g) | avg rewet (g) |
|---|---|---|---|---|---|---|---|---|
| 1 | 9.34 | 0.11 | 7.72 | 7.00 | 9.62 | 25.51 | 32.62 | 10.87 |
| 2 | 10.07 | 0.09 | 7.69 | 7.30 | 10.37 | 31.29 | 38.68 | 12.89 |
| 3 | 9.94 | 0.08 | 8.63 | 3.11 | 10.85 | 25.42 | 28.61 | 9.54 |
| AVG | 9.78 | 0.09 | 8.01 | 5.81 | 10.28 | 27.41 | 33.31 | 11.1 |

Although not wishing to be bound by theory, it is believed that the comparatively low rewet exhibited by the tested samples is more due to the presence of the ADL, the cellulosic matrix form of the absorbent pad, and the SAP, than to the presence of the odor control system components.

Although the present invention has been shown and described with reference to the foregoing operational principles and illustrated examples and embodiments, it will be apparent to those skilled in the art that various changes in form and detail may be made without departing from the spirit and scope of the invention. The present invention is intended to embrace all such alternatives, modifications and variances that fall within the scope of the appended claims.

The invention claimed is:

1. An absorbent article comprising:
   a cellulosic pulp structure comprising a matrix of bleached softwood kraft pulp cellulose fibers and a fluid retention agent, the cellulose fibers comprising an inorganic alkaline earth metal peroxide and a destabilizing acid disposed on the cellulosic pulp structure, wherein the inorganic alkaline earth metal peroxide and the destabilizing acid are separately disposed on the cellulose fibers in discrete alternating lines.

2. The absorbent article of claim 1, further comprising a fluid-permeable top sheet and a fluid-impermeable back sheet;
   wherein the cellulosic pulp structure is disposed between the top and back sheets.

3. The absorbent article of claim 2, wherein the cellulosic pulp structure forms at least a part of an absorbent core disposed between the top and back sheets.

4. The absorbent article of claim 3,
   wherein the absorbent core includes multiple layers, including a storage layer and an additional layer that is interposed between the storage layer and the top sheet and that is adapted to acquire fluid and to distribute acquired fluid to the storage layer.

5. The absorbent article of claim 4, wherein at least the storage layer includes the cellulosic pulp structure.

6. The absorbent article of claim 3, wherein the cellulosic pulp structure forms at least a part of each of multiple layers of the absorbent core, including a storage layer and an additional layer that is interposed between the storage layer and the top sheet and that is adapted to acquire fluid and to distribute acquired fluid to the storage layer.

7. The absorbent article of claim 2, wherein at least the top sheet is hydrophobic.

8. The absorbent article of claim 1, wherein the fluid retention agent comprises a superabsorbent polymer.

9. The absorbent article of claim 1, wherein the inorganic alkaline earth metal peroxide is calcium peroxide.

10. The absorbent article of claim 1, wherein the destabilizing acid is citric acid.

11. The absorbent article of claim 1, having one or more of:
   a peroxide content from about 1% to about 10% by weight of the cellulose fibers; and an acid content from about 0.45% to about 3% by weight of the cellulose fibers.

12. The absorbent article of claim 1, wherein the article is a disposable absorbent article selected from the group consisting of a diaper, an adult incontinent product, a feminine hygiene product, and a bandage.

13. The absorbent article of claim 1, exhibiting one or more of an average rewet lower than about 13 g and a total rewet lower than about 39 g.

14. A method of forming an odor-controlling cellulosic pulp structure, the method comprising:

singulating a bleached softwood kraft pulp cellulose pulp sheet;

forming a matrix with the singulated cellulose fibers;

distributing a fluid retention agent through the matrix of cellulose fibers; and separately drizzling an inorganic alkaline earth metal peroxide and a destabilizing acid onto the matrix of cellulose fibers such that the inorganic alkaline earth metal peroxide and the destabilizing acid are separately disposed on the cellulose fibers in discrete alternating lines.

15. The method of claim 14, wherein the matrix of cellulose fibers is an airlaid pad.

16. A cellulosic pulp structure comprising a matrix of bleached softwood kraft pulp cellulose fibers and a fluid retention agent, the cellulose fibers comprising an inorganic alkaline earth metal peroxide from about 1% to about 10% by weight of the cellulose fibers and a destabilizing acid from about 0.45% to about 3% by weight of the cellulose fibers, wherein the inorganic alkaline earth metal peroxide and the destabilizing acid are separately disposed on the cellulosic pulp structure in discrete alternating lines.

17. The cellulosic pulp structure of claim 16, wherein the inorganic alkaline earth metal peroxide is calcium peroxide, the destabilizing acid is citric acid, and the fluid retention agent comprises a superabsorbent polymer.

18. An absorbent article comprising:

an absorbent core comprising a cellulosic pulp structure comprising a matrix of bleached softwood kraft pulp cellulose fibers and a fluid retention agent, the absorbent core comprising an inorganic alkaline earth metal peroxide and a destabilizing acid, wherein the inorganic alkaline earth metal peroxide and the destabilizing acid are separately disposed on separate layers of the absorbent core.

19. The absorbent article of claim 18, wherein the absorbent core is disposed between top and back sheets of the absorbent article.

20. The absorbent article of claim 19, wherein the separate layers include a storage layer and an additional layer that is interposed between the storage layer and the top sheet and that is adapted to acquire fluid and to distribute acquired fluid to the storage layer.

21. The absorbent article of claim 19, wherein the cellulosic pulp structure forms at least a part of the separate layers of the absorbent core, including a storage layer and an additional layer that is interposed between the storage layer and the top sheet and that is adapted to acquire fluid and to distribute acquired fluid to the storage layer.

* * * * *